United States Patent
Depfenhart (10) Patent No.: US 10,098,782 B2
(45) Date of Patent: *Oct. 16, 2018

(54) LASER THERAPY SYSTEM AND METHOD FOR TREATMENT OF A COLLAGEN STRUCTURE AND OF VARICOSE BLOOD VESSELS IN AN EYE

(71) Applicant: Telesto GmbH, Ulm (DE)

(72) Inventor: Markus Depfenhart, Hamburg (DE)

(73) Assignee: TELESTO GMBH, Ulm (DE)

( * ) Notice: Subject to any disclaimer, the term of this patent is extended or adjusted under 35 U.S.C. 154(b) by 1002 days.

This patent is subject to a terminal disclaimer.

(21) Appl. No.: 14/109,969

(22) Filed: Dec. 18, 2013

(65) Prior Publication Data
US 2014/0171926 A1    Jun. 19, 2014

(30) Foreign Application Priority Data
Dec. 18, 2012    (EP) .................... 12197909

(51) Int. Cl.
*A61N 5/06* (2006.01)
*A61F 9/008* (2006.01)
*A61F 9/007* (2006.01)

(52) U.S. Cl.
CPC ............ *A61F 9/008* (2013.01); *A61F 9/0079* (2013.01); *A61N 5/062* (2013.01);
(Continued)

(58) Field of Classification Search
CPC .................. A61N 5/062; A61N 5/0622; A61N 2005/0626; A61N 2005/0627; A61N 2005/0628; A61N 2005/0635; A61N 2005/0651; A61N 2005/0661; A61N 2005/0667; A61N 2005/067; A61F 9/0079; A61F 9/008; A61F 2009/00821; A61F 2009/00842; A61F 2009/00844; A61F 2009/00851; A61F 2009/00861; A61F 2009/00865
(Continued)

(56) References Cited

U.S. PATENT DOCUMENTS 9,486,284 B2 * 11/2016 Depfenhart .......... A61B 18/203

FOREIGN PATENT DOCUMENTS

WO    2010/093908    8/2010
WO    2012/145159    10/2012

* cited by examiner

*Primary Examiner* — Ahmed Farah
(74) *Attorney, Agent, or Firm* — Mark M. Friedman (57) ABSTRACT

The present invention refers to a Laser therapy system and a method for treatment of a sclera/conjunctiva of an eye, comprising:
 a dispenser for a photosensitizer agent;
 a 3D imaging unit;
 an image processing unit being adapted to recognize the collagen tissue structure and to determine a thickness thereof;
 a UVA light source being adapted to a crosslinking of the collagen tissue;
 a second Laser light source being adapted to be absorbed mainly by varicose blood vessels;
 an optical system for deflecting and focusing the UVA light and the second Laser light on a focus point within the sclera/conjunctiva;
 a processing and control unit being adapted to determine a target thickness and a thickness deviation;
 a pattern for an application of the UVA light energy;
 a UVA light energy to effect a growth of the collagen tissue structure until the target thickness is achieved.

15 Claims, 5 Drawing Sheets

(52) U.S. Cl.
CPC . *A61F 9/00821* (2013.01); *A61F 2009/00842* (2013.01); *A61F 2009/00851* (2013.01); *A61F 2009/00853* (2013.01); *A61F 2009/00865* (2013.01); *A61N 2005/0661* (2013.01)

(58) Field of Classification Search
USPC .......... 606/4–6, 10–12; 607/88–92; 128/898
See application file for complete search history.

LASER THERAPY SYSTEM AND METHOD FOR TREATMENT OF A COLLAGEN STRUCTURE AND OF VARICOSE BLOOD VESSELS IN AN EYE

The present invention refers to a Laser therapy system and a respective method for a treatment of the eye comprising a 3D imaging unit for imaging a tissue structure of the sclera and/or conjunctiva of the eye, a UVA and another Laser light source with an optical system and a processing and control unit to deflect and focus the UVA and the Laser light precisely on the tissue structure. The Laser therapy system is usable for a rejuvenation of the tissue structure of the sclera and/or conjunctiva by inducing a physiologically and anatomically precise crosslinking and growing of new collagen and by disintegrating varicose vessels in the sclera and/or conjunctiva. The application is a kind of an "eye-bleaching".

BACKGROUND OF THE INVENTION

The cornea and sclera make up the outer tunic of the eye. Each is a connective tissue containing collagen fibrils embedded in a proteoglycan-rich extrafibrillar matrix, wherein the cornea is uniquely transparent and the sclera is totally opaque. Both tissues require strength to maintain the excess pressure within the eye and to resist external knocks and forces applied by extraocular muscles during eye movement. The mechanical strength is provided by deposition of collagen in a lamellar structure, wherein the lamellae run parallel to the surface of the tissue. The sclera as the white part of the eye is a tough connective tissue and is continuous with the cornea. Scleral collagen is, in composition and arrangement, similar to that of normal skin, with wider fibrils and much more interwoven structure than in the cornea. The sclera has no optical role other than to provide support for the retina on the back of the eye, but it has important physiological functions as providing fluid outflow channels and mechanical functions in maintaining an eye shape. The limbus constitutes the border between the cornea and the sclera. Changes of the collagen structure of the sclera and conjunctiva are accompanied by a development of shortsightedness (myopia). The above-mentioned relationships are e.g. taught by K. M. Meek, Chapter 13, The Cornea and Sclera, pages 359 ff., of P. Frantzl (ed.) Collagen Structure and Mechanics, Springer 2008, ISBN: 978-0-387-73905-2.

Methods and apparatuses for a rejuvenation of human skin are known for example by names such as Needling method, a Laser therapy method, fractionated Laser ablation, or percutaneous collagen induction method. For the fractionated Laser ablation devices such as Fraxel®, for instance, are known and in use. A denaturation of collagen and, consequently, a "shrinking" of the tissue can also be achieved by radio frequency, for instance by a Thermage® device. Such methods and devices are generally based on an application of injuries in the skin by means of a mechanical or a thermal therapy device, wherein the injuries are followed by subsequent repair processes causing also a reconstitution of the collagen structure in the skin with its natural structure. A degradation of the destroyed tissue and the reconstitution of the collagen tissue rejuvenate the skin in its biomechanical and aesthetical properties. The current fractional Laser based methods with a focused Laser beam do preferably not destroy a surface of the skin, but as in meso-therapeutic methods or in percutaneous collagen induction therapy, also called "needling" as a perforation of the skin, there are certain disadvantages such as increased infection risk for the patient as well as for the therapist. With the Laser treatment methods a better control of the results can be achieved compared with the mechanical percutaneous methods and the current fractional Laser based methods. However, in both cases, micro bleedings in the stratum papillare of the skin are produced, either by means of a needle roller or by a light-induced perforation of end-arterioles in the skin. The micro bleedings cause a release of blood corpuscles and mainly thrombocytes from the perforated end-arterioles. From the thrombocytes, among others, growth factors, such as TGFβ3, VEGF, EGF, for example, are released. The growth factors promote the degradation and regeneration of degenerated dermal collagen as found in aged individuals or pathologically in scars. The so caused formation of directed collagen in the dermis results in a regeneration or rejuvenation of the skin to a certain degree. The above-mentioned treatment methods advantageously include a perioperative topical treatment with creams containing high doses of vitamins, as substantially vitamin C for achieving high local vitamin levels in the skin. Vitamin A and C are important cofactors or coenzymes for the formation of collagen and elastin in a target region of the skin for forming collagen and elastin.

Another coexisting method for skin rejuvenation and also for the sclera and conjunctiva is increasing a crosslinking between the single collagen fibers within the collagen structure of the skin, which gives the collagen tissue a rejuvenated and biomechanically much better elasticity and strength. Such an increase of the crosslinking between the single collagen fibers can be induced by a pretreatment of the skin with a Photosensitizer like Riboflavin containing and skin penetrating agent in combination with UVA light which activates a process similar to a lysyl oxidase process. Lysyl oxidase is an extracellular copper enzyme that catalyzes formation of aldehydes from lysine residues in collagen and elastin precursors. The aldehydes are highly reactive, and undergo spontaneous chemical reactions with other lysyl oxidase-derived aldehyde residues, or with unmodified lysine residues. This results in crosslinking of collagen and elastin, which is essential for stabilization of collagen fibrils and for the integrity and elasticity of mature elastin and, last but not least, for the skin. Complex crosslinks are formed in collagen and in elastin that differ in structure (source: Wikipedia). Crosslinking takes place in such a way that end parts of the collagen fibrils are connected with each other in a kind of a covalent connection, wherein the space between the collagen fibrils becomes shorter causing a contraction of the collagen tissue in that region. In other words, if the collagen tissue is contracted in the x/y direction and parallel to the skin surface the collagen tissue also grows in its thickness in an orthogonal z direction. An application of a photosensitizer agent containing e.g. Riboflavin in combination with an UVA light stimulates a process similar to the lysyl oxidase process and therefore the crosslinking.

EP 1 2177 266 A1 of the author of the present invention discloses a Laser therapy system for rejuvenation of the skin via a combined treatment of a first UVA light treatment for collagen crosslinking together with a second Laser light treatment with another light source for a subcutaneous Laser needling application. The integrated optical system allows a precise placement of the focus point or light spot, respectively, of the first UVA light and of the second Laser light treatment.

DE 10 2010 022 634 A1 discloses an ophthalmologic Laser therapy system comprising a pulsed Laser light source, a controllable optical system, a Hartman-Shack sensor and a control unit controlling a position of the laser light pulse and its energy, such that the Laser energy pulses can be controlled in space and energy so as to achieve determined and constant therapeutic results.

DE 10 2010 020 194 A1 discloses another ophthalmologic Laser therapy system substantially comprising another Laser light source, a controllable optical system, a detector unit and another control unit, wherein the system allows diagnosis of the cornea, laser cutting as well as a soft light treatment for stabilizing the cornea. For the stabilizing of the cornea or cuts within the cornea, respectively, the document teaches a treatment of said cuts with UVA light, such that collagen growing is induced and closes the cuts at least partly. However the UVA light is applied without taking a microstructure of the collagen into account, and it is believed that rather a crosslinking than a growth of new collagen takes place.

WO 2009 033 083 A1 gives a generic view of possible treatments and reactions of the sclera, conjunctiva and the cornea. Treatment of myopia and hyperopia by surgical techniques including corneal interventions, such as reshaping a surface curvature of the cornea, and of non-corneal manipulations, such as altering properties of the sclera, a ciliary muscle, zonules, or the lens, is described. Also a cutting of kerfs into portions of the sclera to improve the accommodation possibility is disclosed. However this increases the risk of infections. A generating of a low-level radiation is preferred for the treatment of the sclera and the ciliary muscle to improve a refraction of the eye, with a light energy not ablating tissue from the sclera or the ciliary muscle. In this document effects are described rather than a controlled collagen growth within the sclera, conjunctiva or cornea.

EP 2 108 347 A1 discloses another ophthalmologic Laser therapy system for a controlled cornea ablation, wherein a surface and thickness of the cornea is detected by an optical coherence tomography system (OCT) and a Laser light beam generated which is time-, energy- and space-controlled. Thus certain regions of the cornea with irregularities are detected via the OCR and controllably ablated by the Laser beam. The OCR imaging system has a resolution of some 10 μm in x/y direction and 3 μm in the z direction orthogonally to the surface of the cornea. The process of detecting, controlling and generating the Laser beam happens in real time. However the process takes only an ablation of cornea tissue into account but not a growing of new tissue. A shaping by the crosslinking of the collagen tissue is not mentioned, either.

WO 2007 082 127 A2 discloses a combination therapy for a long lasting controlled cerato-reformation (CRK), comprising a measurement of the total corneal topography, an ablation of parts of the cornea and an UVA light treatment for new collagen growth. For the UVA light induced collagen growth a photosensitizer is applied as Riboflavin (C3-R) in the form of eye drops which increases the amount of collagen crosslinking in the cornea. Thus the biomechanical rigidity of the cornea is taught to be increased. The light intensity is selected to be 3 mW/cm$^2$, the wavelength is 365 nm and the time is 30 minutes.

US 2012 059 439 A1 discloses an aberration control by induced new collagen crosslinking combined with a beam shaping technique. It is taught that new collagen crosslinking is used to alter a characteristic of the cornea, such as thickness or refractive index to correct wavefront aberrations. The light intensity is 3 mW/cm$^2$ and the wavelength is 365-370 nm. However, the UVA light is applied rather as a wide beam over an area of a certain part of the cornea and not as a focused light beam describing a pattern. Also, a tightening of the outer sclera to give the eyeball a corrected shape is not mentioned.

The induction of the crosslinking of the collagen by the UVA light must also be seen in connection with the fact that the UVA light has a cell toxic effect as well. So, the UVA energy or density, respectively, has to be reduced as much as possible, such that the desired rejuvenating effect is still achieved but with the least toxic effect possible. It seems that the mentioned methods and devices of the prior art do not sufficiently take into account the toxic effect of the UVA. According to the prior art the UVA light is applied with a relatively wide beam diameter in relation to the microstructure of the collagen with the collagen fibrils and the collagen fibril bundles.

Taking into account the microstructure of the collagen as a network of the collagen fibers and the process how the crosslinking is induced by the UVA light in combination with the photosensitizer, the UVA light should be applied as a focused light beam with the focus point describing a pattern within the microstructure of the collagen tissue so as to reduce the total UVA light energy per mm$^2$ or mm$^3$ for a certain crosslinking. Preferably the pattern of the focus point should be adaptable to an orientation of the collagen within a certain collagen layer. In other words, the UVA light energy should be focused on certain points or paths within a plane or within a spherical plane within the pattern, wherein the pattern comprises areas between the paths or points which are not irradiated with UVA light, such that the percentage of the non-irradiated areas could be seen as a reduction of total applied UVA energy. Furthermore, the crosslinking could preferably be controlled by a kind of a micro-treatment instead of a broad and general treatment according to the prior art. Such a micro-structural growth could also open up new possibilities of a refractive eye treatment.

The new collagen structure induced by the UVA light grows along existing collagen fibers of the collagen tissue. Also an orientation of the new collagen fibers is the same as that of the underlying existing collagen fibers. The UVA light induced growth of the new collagen structure requires a certain UVA energy density at the respective collagen fiber or more precisely on a surface of a collagen layer on which the new collagen structure grows.

Furthermore, the therapy of the whitening of the sclera and/or conjunctiva could be enhanced taking also a Laser needling therapy into account as it is known from treatments of normal skin. For the Laser Needling particularly the end-arterioles have to be made permeable for the corpuscular blood cells such that a further growth of additional new collagen is stimulated. This kind of stimulation can be achieved by a pulsed and focused Laser light beam with a focus point at the end-arteriole, by a Laser ablation or by a light energy strong enough to induce an optical breakdown. At least a capillary leak through protein denaturation of the vascular endothel shall be caused. The Laser Needling could also be used to weld varicose vessels in the sclera.

With regard to the rejuvenation of the sclera and/or conjunctiva under aesthetical aspects with the objective to whiten the eye the treatment could also take into account a combined treatment of the UVA light therapy and a kind of a Laser treatment for destroying varicose blood vessels. Advantageously the Laser therapeutic device should have both treatment possibilities integrated therein, such that a combined treatment could take place within a same treatment session.

Moreover, by inducing the crosslinking and the growth of the new collagen it is imaginable that said crosslinking and growth of the new collagen could be determined, such that the refractive system of the eye with an astigmatism could be corrected and Myopia and Hyperopia could be treated.

For clarity reasons the eye is to be understood as a living eye. The wording UVA light is equivalent to the wordings UVA energy or energy density, whatever is correct in the respective sense which is apparent to a person skilled in the art. The UVA light can also be a Laser light. The term collagen is equivalent with collagen tissue and collagen fibers or collagen fiber bundles, whatever is correct in the respective sense which is apparent for a person skilled in the art.

SUMMARY OF THE INVENTION

The objective of the invention is to overcome the shortcomings explained above and to provide a Laser therapy system for rejuvenation of the eye and in particular of a sclera and/or conjunctiva, such that a crosslinking of collagen and growth of new collagen can be stimulated locally as precisely as possible and by as little UVA light energy as possible.

Another objective of the invention is to enable the Laser therapy system for a precise disintegration of varicose vessels within the sclera and/or conjunctiva without destroying an outer surface of the eye and preferably in a computer assisted controlled way.

The above objectives as well as further objectives which will also become apparent from the following description are achieved by a Laser therapy system and a respective method for an eye treatment according to the features mentioned in the independent claim 1 or 16, respectively. Additional advantageous features and characteristics of the invention are set forth in the dependent claims and in the detailed description.

Advantageously, the Laser therapy system comprises an imaging unit for 3D imaging of an imaging volume of the sclera and/or conjunctiva in combination with an image processing unit which is adapted to detect a collagen tissue structure within the imaging volume. The image processing unit recognizes the collagen tissue structure and is able to detect a thickness thereof. The recognition of the collagen tissue structure allows a treatment adapted thereto, such that a micro-treatment with a focus point of a focused UVA light beam allows a more precise treatment with less total applied UVA energy than in the conventional way according to the prior art. Thus a certain pattern described by the focus point with the applied UVA light energy can be generated within the sclera and/or conjunctiva, such that the pattern comprises preferably different planes, wherein the focus point is positioned or moved in paths, preferably parallel to the skin surface. The term "skin" is meant to designate the sclera and/or conjunctiva.

Furthermore the imaging unit and the image processing unit are preferably capable of recognizing collagen layers and of distinguishing between different collagen layers having a different orientation, wherein the orientation may be either longitudinal, transverse or diagonal with respect to a preferred direction. Thus, the certain pattern for the UVA light application is even better adaptable to the existing and natural local collagen tissue structure of the sclera and/or conjunctiva. Furthermore, the pattern is better adaptable to the different collagen layers with the respective orientation in the different heights; this improves the natural crosslinking and growth of the collagen.

The focusing of the UVA light is such that the focus point with the respective UVA light energy describes a pattern, which, in contrast to a broad and unspecific application of the UVA light energy, allows a reduction in the total UVA light energy application, compared with an application of a light beam which spreads the respective energy more homogeneously over the local area of sclera and conjunctiva. Also, the adaptation of the pattern to the collagen structure and preferably to the orientation of the respective collagen layer allows an additional reduction in the total UVA light energy application. The light intensity of the focused light beam can be smaller and still reaches its necessary intensity and energy, respectively, in the focus point to induce the crosslinking and a generation of new collagen, compared with the uniformly spreading light beam.

Also the high light intensity in the focus point can be applied exactly where it makes sense from a physiological point of view, such that collagen layers can be crosslinked, layer by layer, preferably adjacent and parallel to each other. Advantageously and preferably the plane or spherical plane wherein the focus point is moved in steps or in paths is elevated upon the respective layer that has been treated with the respective UVA light energy, such that one new collagen layer in a sense of its structure is to be grown on top of a previously treated new collagen layer. It is to be mentioned that with the new collagen layer also a new structure of the previously untreated collagen layer is meant. Using the photosensitizer as an agent for the skin and matching it with UVA light, said growth of the new collagen is even more increased, or the UVA light energy applied can be decreased. Thus cytotoxic effects of the UVA light can be reduced as much as possible. Preferably the amount of the newly generated or induced crosslinks which cause a growth of the thickness of the collagen tissue structure is predicted or determined by an expert data base giving an indication for a growth factor for the thickness of the collagen structure due to the crosslinking as a function of the applied UVA light energy, the pattern and of patient parameters, to name some obvious factors. The growth of the thickness of the collagen tissue structure is caused by a tightening of the collagen structure, as mentioned before, caused by a tightening of the respective end-parts of the respective single collagen fibrils of the collagen tissue structure. Said Laser therapy system allows changing the collagen structure, wherein the collagen structure becomes preferably tighter and denser, also getting more dense in an optical sense, meaning that the new collagen structure reflects more outer light and therefore is whiter. The choroid is better covered by the new collagen structure which appears white.

Advantageously the Laser therapy system comprises also another second light source being a Laser and preferably an IR Laser, which allows the surgeon to disintegrate varicose blood vessels and to apply a Laser Needling treatment as well. Thus the patient does not have to be moved or readjusted, no unnecessary time is lost, and the same man-machine interface can be used by the surgeon or user and no adaptation effort of the user has to be invested. Also most of the components therein can be reused such as the imaging unit, preferably the image processing unit, the optical system and the processing and control unit which are high-tech equipment and very expensive.

Using the second light source for the Laser Needling treatment, more growth of naturally growing collagen can be induced. As well varicose blood vessels can become welded or disintegrated. The growth of the new collagen induced by the Laser Needling method is determinable by an expert data base giving an indication of a respective growth factor for the new collagen preferably as a function of perforations of blood vessels as end-arterioles per mm$^2$ or per mm$^3$ or the like. The Laser Needling method is preferably applied where the collagen structure has become thin and weak. The Laser Needling treatment induces a more delayed but very natural collagen growth with a long lasting effective rejuvenation. Furthermore the second Laser light can also be used for cutting out parts of the cornea or sclera. Thus, the combination of treatment methods via the UVA light and via the second Laser light gives the surgeon a complete set of treatment possibilities needed.

The image processing unit allows a recognition of tissue structures and preferably of different collagen layers which are adjacent or lay on top of each other, such that the respective focus point can be directed exactly within a plane at the outer surface of a collagen layer in an automatic or semi-automatic controlled way. Taking preferably the microstructures of the respective collagen layer into account, the focus point with the respective light energy is preferably directed within a determined plane or spherical plane in a fast and automatic manner according to a predefined pattern. Furthermore, such a micro-treatment is also only possible in an automatic or semi-automatic way, and would not be possible manually within a reasonable time limit. This becomes also evident in view of the UVA light treatment generating predefined patterns with thousands of single light spots within said focus points per mm$^3$.

One of the advantages shall be emphasized again, which is a reduction of the total UVA light energy applied to the skin for a certain treatment effect, such that the cytotoxic effect of the UVA light can be reduced as much as possible.

Advantageously a cross-sectional area of the entry of a focused light beam into the sclera or conjunctiva is by a stronger factor than the cross-sectional area of the focus point, wherein the factor is preferably larger than 10 and more preferably larger than 100. This prevents damaging the skin above and below the focus point, wherein still enough light energy is applied in the focus point.

With regard to the image processing unit, the UVA light treatment can be applied in a more automatically controlled way and in a way of micro-treatment which would not be possible by traditional manual treatment practices in a reasonable treatment time. Thus the treatment time can also be reduced relative to the traditional manual treatment practices, reducing the treatment costs as well.

Preferably a refractive change of an optical system of the eye can also be determined by the change of the collagen tissue structure, such that the treatment with the UVA light and the Laser Needling treatment can take such a refractive change into account, either as a side effect or as a desired aim to improve also a sharp sight of the eye.

Further advantageous aspects of the invention are set forth in the following detailed description.

One solution of a preferred embodiment according to the present invention is disclosed in the following drawings and in the detailed description but it shall not be limiting the invention.

DETAILED DESCRIPTION OF A PREFERRED EMBODIMENT OF THE INVENTION

Figure 1:
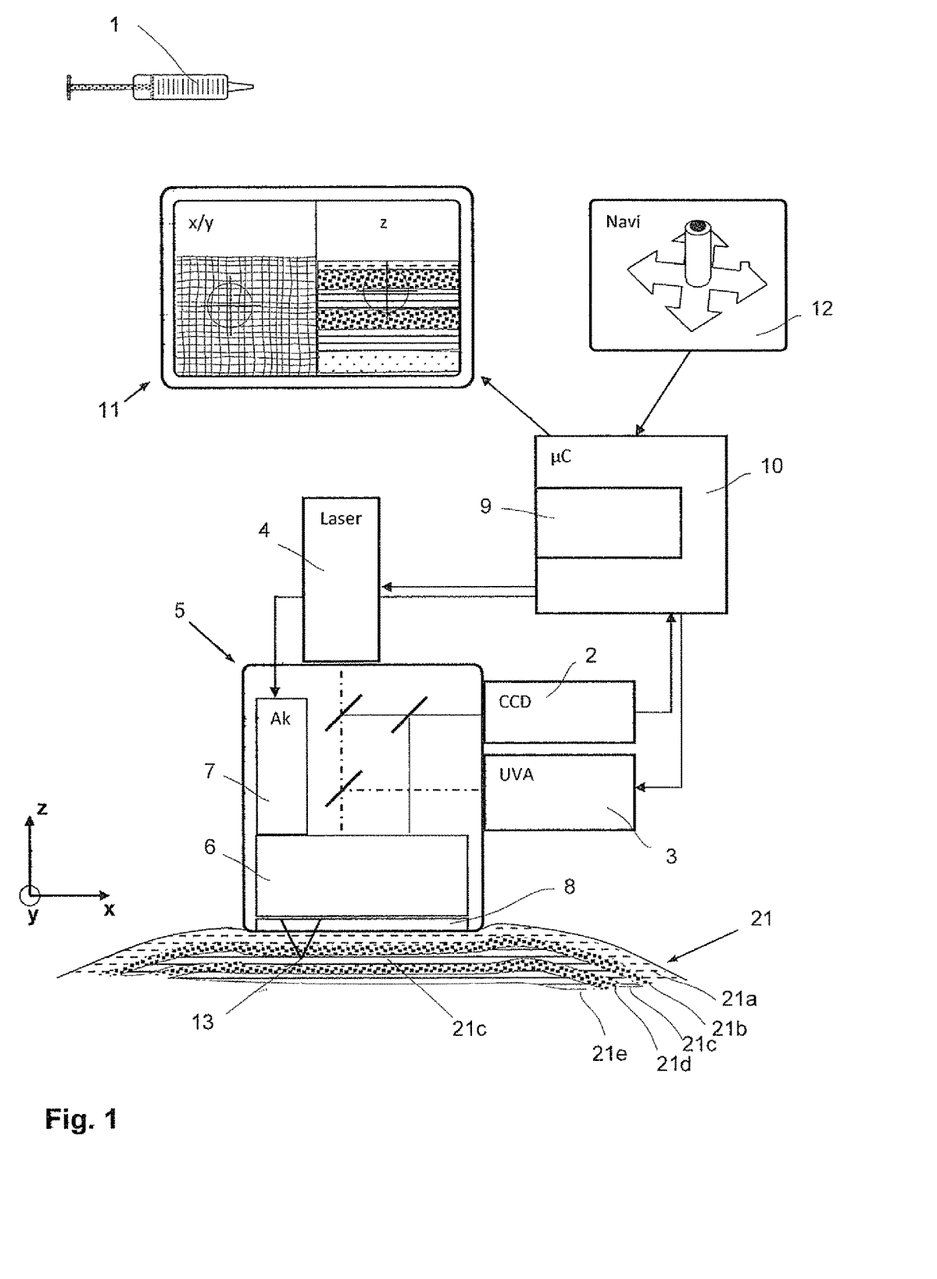
FIG. 1 is a schematic drawing of the Laser therapy system with a UVA light source, with another light source, with an optical system connected to a part of an eye, with a screen and a navigation control input device and a separate dispenser for a photosensitizer containing agent.

FIG. 1 shows a schematic diagram of the laser therapy system for an eye treatment and in particular for a treatment of the sclera and/or conjunctiva 21 of a living eye 20 according to a preferred embodiment of the invention. For the sake of clarity the sclera and/or conjunctiva 21 are generally meant to indicate at least a part of said sclera and/or conjunctiva 21. For the sake of simplicity the sclera and/or conjunctiva 21 are also simply called skin in the following.

According to the invention, the Laser therapy system comprises a dispenser 1 such as a syringe, for example, containing an agent for an application on the skin, wherein the agent contains a photosensitizer for mediating a collagen and elastin crosslinking in a targeted manner during an UVA light irradiation. For the sake of simplicity the term collagen preferably also comprises elastin. Generally the word collagen also stands for a tissue or tissue structure of collagen fibers forming the collagen structure as a network of a plurality of connected collagen fibers. The agent is preferably a cream, a gel or liquid with a skin penetrating effect and it contains preferably riboflavin (vitamin B2), coenzymes, vitamin A, vitamin E, or vitamin C or a combination thereof for a synthesis of the collagen and elastin in the skin. Preferably the agent is a photosensitizer. Preferably at least the mucosa is penetrated by the agent. Preferably the photosensitizer containing agent comprises also fluorescent properties for determining a penetration depth in the skin. As described before, the photosensitizer agent and the UVA light wavelength are matched with each other, such that with as little as possible UVA light energy a reaction similar to the lysyl oxidase reaction takes place in the skin activating a crosslinking between end-parts of the single collagen fibers and tightening the collagen structure as it was when the patient was younger. Also imaginable is that the dispenser 1 is no separate device but instead an integral part of the Laser therapy system. Further it may comprise a sensor for determining a certain quantity of the applied agent.

The Laser therapy system further comprises an imaging unit 2 for a 3D imaging of the skin or respectively of a volume thereof, wherein the imaging unit 2 is coupled to the skin by an optical system 5 with an aperture 8. The aperture 8 has preferably a function as an inlet for light coming from the skin which is preferably a reflected light and preferably another function also as an outlet for a possible illumination light for illumination of the skin. Thus a volume of the skin is imaged and respective image data is output. The optical system is preferably controllable in such a way that different volumes of the skin can be imaged within a same position of the aperture 8 relative to the eye. Preferably the illumination brightness, the contrast and the like are controllable by another connected component of the Laser therapy system. Preferably the imaging unit 2 is based either on an Optical Coherence Tomography (OCT), a fluorescence or self-fluorescence microscopy, a fluorescence or self-fluorescence tomography, a light reflection or a light extinction measurement or a combination thereof. Preferably the imaging unit 2 is a CCD sensor. Preferably the imaging unit 2 works with at least two wavelengths for a better discrimination between the collagen and blood vessels. Preferably the imaging unit comprises also at least one polarization filter. A different kind of imaging unit 2 according to the prior art is also imaginable. Preferably a monitor with a screen 11 is connected to the imagining unit 2 either directly or via an image processing unit 9 or a different processing and control unit 10.

The Laser therapy system further comprises the image processing unit 9 which is preferably connected to an output of the imaging unit 2 receiving and further processing the image data of the imaging unit 2. It is also imaginable that the image processing unit 9 receives the image data via the processing and control unit 10. Possibly the image processing unit 9 is also part of the processing and control unit 10, as for example a software module or as a separate hardware module or both. The image processing unit 9 is adapted to recognize the local collagen tissue structure and to determine a thickness 36 of the local collagen tissue structure. The thickness 36 of the local collagen tissue structure is a function of a position as it may vary within the skin of the eye 20. The image processing unit 9 recognizes preferably also one or more different adjacent collagen layers within the skin, wherein the different collagen layers are preferably arranged on top of each other like a sandwich. The image processing unit 9 enhances preferably also a displayed image on the screen 11 by contrasting the displayed image. For example, the different collagen layers and other tissue structures could be given different colors, could be displayed with an enhanced contrast or the like. The image processing unit 9 recognizes preferably also an orientation of the respective collagen tissue or fibers or collagen fiber bundles within the respective collagen layer, wherein the detection of the orientation allows the Laser therapy system to treat the skin in a more physiologically correct manner, such that an applied pattern of the UVA light energy for a local small area is aligned with said orientation of the collagen fibers in that local area. Said alignment is preferably parallel or perpendicular to the orientation or aligned in a different way according to certain expert know-how.

The Laser therapy system further comprises an UVA light source 3, which is controllable and which generates a UVA light. The UVA light source 3 is connected to the optical system 5, wherein the UVA light is controllably deflected and focused on a focus point 13 behind the aperture 8 and in the skin. The focus point 13 of the UVA light can be deflected and focused by the optical system 5, such that the focus point 13 can be controlled in all three directions within at least a part of the imaging volume, wherein the part is preferably 30% or 50% or even 100% of the imaging volume. The UVA light has a wavelength and an intensity which is adapted to the collagen crosslinking and a collagen growth in the skin in combination with the photosensitizer agent. Preferably the wavelength and the intensity are matched with the photosensitizer agent and the skin for a most efficient photochemical effect and the collagen growth, after all. The UVA light has a wavelength of preferably 340-450 nm and an intensity of preferably 100 $\mu$W-100 mW or alternatively an energy output of 2-10 Joule/cm$^2$ or more preferably 0.8-2 Joule/cm$^2$ or even more preferably 0.1-0.8 Joule/cm$^2$. Alternatively the wavelength of the UVA light is 300-450 nm. Or preferably the wavelength is about 260-290 nm, and more preferably 275-285 nm. Another preferable wavelength is about 370 nm. Preferably the UVA light source 3 is a Laser such as for example an LED laser diode. Preferably the UVA light source 3 is also controllable in its light intensity or energy or both. Preferably it can be pulsed, such that a defined light energy is applicable to the skin. Laser pulses can be in a range of fs-$\mu$s, but also pulses in the range of ms-s are imaginable. To use a continuous light is also imaginable which is positioned and moved with its focus point 13 by the optical system 5 along certain paths in the skin.

The Laser therapy system further comprises a second light source which is a controllable Laser light source 4, generating a second light with a second wavelength and a second intensity. Preferably a switchable Laser is used. The Laser light source 4 is connected to the optical system 5, wherein the second light is controllably deflected and focused on the focus point 13 behind the aperture 8 and in the skin. The focus point 13 of the second light can be deflected and focused by the optical system 5, such that the focus point 13 can be controlled in all three directions within at least a second part of the imaging volume, wherein the second part is preferably 30% or 50% or even 100% of the imaging volume.

The second wavelength, the second light intensity, a second pulse duration and a second pulse frequency or repetition rate, respectively, of the second light source 4 are preferably adapted for a good absorption of the second light in the focus point 13 within the skin. The second light is preferably adapted for releasing energy in the focus point 13 so as to make the end-arterioles permeable, preferably in a targeted manner with as little collateral damage as possible. Preferably, Laser parameters are adapted and set in such a way that in the focus point 13 in the skin either a thermal, a photoablative or a plasma-induced reaction is produced. The second wavelength is preferably 450-550 nm, particularly preferred 550-650 nm or 650-800 nm or 800-2000 nm in the IR range. The second wavelength is preferably selected and set such that the second wavelength is absorbed particularly well by blood vessels and by hemoglobin and as little as possible by the other tissue of the skin. The second light intensity preferably corresponds to 1 mW-100 W as a focused light beam. The second pulse duration preferably is 10 ps-100 $\mu$s, but it can also be set to be shorter or longer.

The optical system 5 comprises an optical deflection and focusing unit 6 which is preferably controllable by an actuator unit 7 and deflects and focuses the UVA light of the UVA light source 3 and the second light of the Laser light source 4 on the focus point 13 behind the aperture 8 and in the skin. The actuator unit 7, which is preferably an integral part of the optical deflection and focusing unit 6, is controllable by electrical signals from the processing and control unit 10. The optical deflection and focusing unit 6 deflects and focuses the UVA light and the second light on the focus point 13, such that it is controllably positioned behind the aperture 8 in said imaging volume. The aperture 8 of the optical system 5 comprises preferably an adapter plate which is intended to be positioned on the skin preferably with an optical coupling liquid or coupling gel 8c in between.

Figure 5:
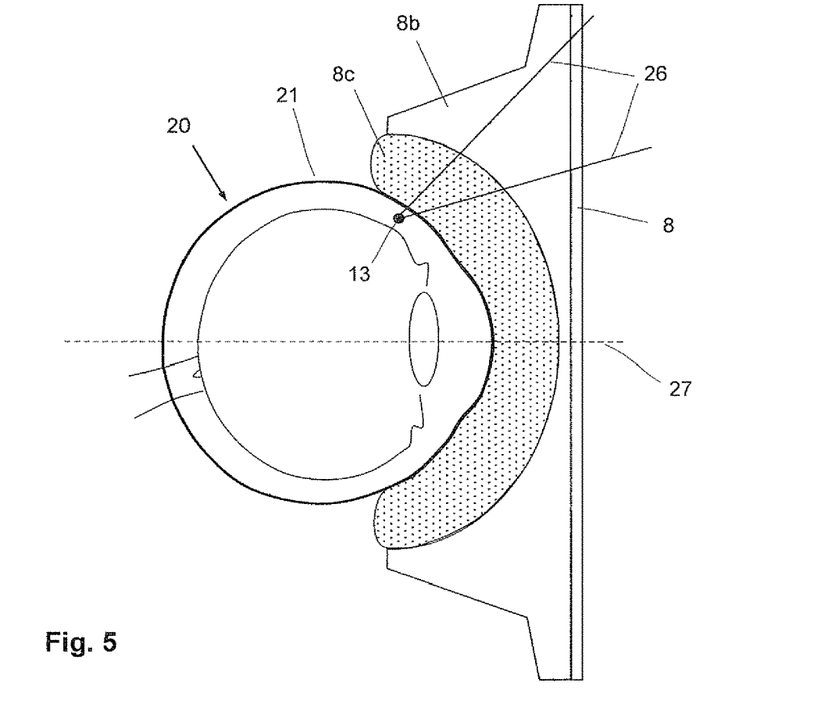
FIG. 5 is a schematic drawing of the eye from a side view with a contact lens connected thereto between the eye and an aperture and with an additional coupling gel to the eye.

FIG. 5 shows the adapter plate connected to the eye 20 as a contact lens 8b, wherein an optical path 26 of the UVA light is shown with the focus point 13. Preferably the contact lens has a concave shape adapted to the eye 20. More preferably the contact lens 8b is optically connected to the eye 20 by a flexible pocket with a liquid, by a liquid or by a coupling gel 8c having a functionality as an optical coupling. Preferably the adapter plate or the contact lens 8b comprises a plurality of layers which are connected with each other as integral or a non-integral parts. Preferably the contact lens is either of glass or the coupling gel 8e. The coupling gel is preferably an immersion liquid. Preferably the immersion liquid contains Riboflavin. Via the coupling gel or the immersion liquid a resolution of the image and of the treatment can be increased and a damage of the surface of the eye can be decreased. Preferably the coupling gel or the immersion liquid is pumped into the gap between the eye and the aperture 8. Thus the light path is adapted to a more ideal light path.

Alternatively and/or additionally the aperture 8 comprises a surrounding ring shaped means or container being adapted to be placed on the eye and to be filled with the immersion liquid above the eye, such that the UVA light or the second light is led from the aperture 8 through the immersion liquid towards the eye. Preferably the immersion liquid is a tear fluid. Preferably the immersion fluid comprises Riboflavin.

The photosensitive substance as e.g. Riboflavin serves as well as another immersion means that diffuses into the mucosa of the conjunctives and/or sclera. By using the immersion liquid, as explained above, the optical distance between the objective lens and the image depth is optimized in a sense of a more linear optical path function. Aberrations caused by an adjustment of errors of the diffraction index of the optic system remain constant along the optical axis and the photosensitive substance can be exposed in the entire writing area with identical focus and/or patterns of intensity. Preferably the optical system has a high numerical aperture of at least 0.4 and more preferably of at least 0.6. The treatment depth is preferably between 0.001 and 2 mm below the surface of the sclera or conjunctiva 21.

Preferably a connecting part of the adapter plate to the eye 20 is soft such as to achieve connecting forces smaller than would substantially change the refractive system of the eye 20.

Figure 6:
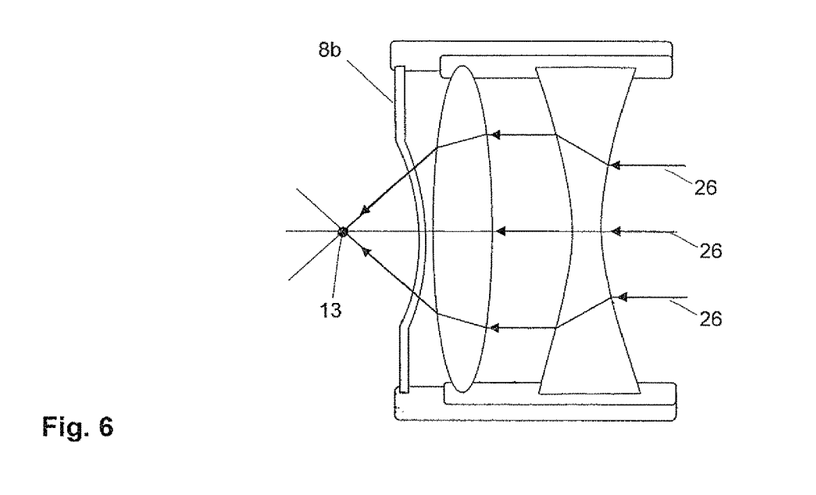
FIG. 6 is a schematic drawing as a side view of another contact lens with a lens system.

FIG. 6 shows from a side view another preferred contact lens 8b with a lens system in front of the contact lens 8b. Said lens system comprises preferably a concave or biconcave lens or the like for enlarging the light beam diameter and a convex or biconvex lens or the like to focus the light beam to the focus point 13. The light path 26 is shown as an example. Said lens system comprises preferably a liquid lens which is fast adaptable. Preferably the lens system is adjustable to the focus point 13 via Piezo actuators. Preferably the lens system is moveable in respect to the contact lens 8b along its optical axis.

Preferably the aperture 8 is part of a movable arm or head which is optically connected with the optical system 5, such that the aperture 8 is controllably moveable over the skin either manually or controllably actuated by the processing and control unit 10.

The UVA and the second light which enters the skin behind the aperture 8 or the adapter plate, respectively, has a first cross-sectional area of preferably 1-30 mm$^2$, which, however, can also be larger. A second cross-sectional area of the focus point 13, also called light spot, has a diameter of preferably 10-100 μm. The diameter of the second cross-sectional area can also reach 1 mm. The factor between the first and the second cross-sectional area is preferably about 1-10 and more preferably about 10-100 and even more preferably between 100-1000. Said factor may also change between the UVA light and the second light application. The depth of the focus point 13 behind the aperture 8 in the skin is controllable preferably in a range of 0.03-3 mm or more.

The processing and control unit 10 is adapted to control the deflection and focusing unit 6 of the optical system 5 and to control the position or the path of the focus point 13 either by a manual input via a navigation control input means 12 or in an automatic way along determined positions or paths, or semi-automatically via both means. The navigation control input means 12 may be a joystick with buttons, a keyboard, a touch pad, a mouse or a combination thereof.

The processing and control unit 10 determines a target thickness 37 for the thickness 36 of the recognized collagen tissue as another function of the position. The target thickness 37 is preferably a mean value or a maximum value of the thickness 36 along a circular ring shaped area 22 around a center axis 27 of the eye 20, see FIG. 2, upper part, for illustration. Other ways of determining the target thickness 37 are also imaginable. Further a thickness deviation 38 is determined or calculated as a difference between the target thickness 37 and the thickness 36, also as a function of the position. Preferably all positions are calculated in plane or spherical polar coordinates. The local positions within the imaging volume may also be calculated and shown on the screen 11 in Cartesian coordinates, but polar coordinates are preferred. For the sake of clarity, again, the term "plane" comprises also spherical planes in this description.

Figure 3:
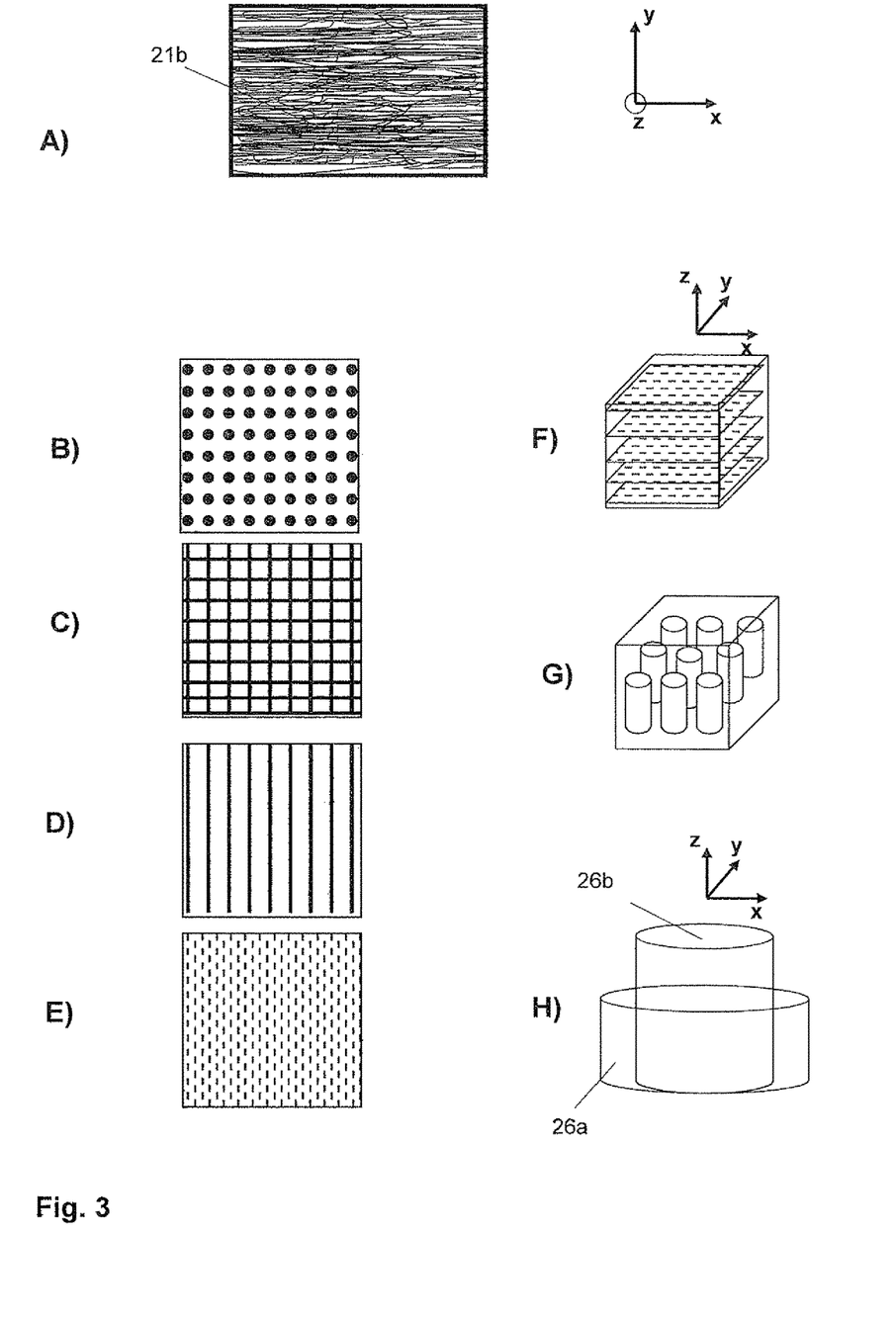
FIG. 3A is a schematic drawing of a top view of a collagen layer of the sclera or conjunctiva.
FIGS. 3B-G are schematic drawings of different patterns for an application of UVA light energy in the sclera and/or conjunctiva.
FIG. 3H is a schematic drawing of a skin volume before and after a treatment with the UVA light energy.

Now, the processing and control unit 10 determines a UVA light energy as a function of the position, such that the UVA light energy applied to the skin causes the respective growth in thickness 36 of the collagen tissue structure, such that the collagen tissue structure is assumed to reach the determined target thickness 37. The UVA light energy is calculated as a function substantially of the thickness deviation 38, the pattern and a growth factor for the thickness 36 of the collagen tissue. At this point it should be mentioned again that the growth in thickness 36 takes place by the UVA light induced crosslinking, wherein the collagen tissue is tightened and shrinks preferably on a horizontal plane parallel to the respective collagen layer and parallel to the surface of the skin. Thus, as the volume remains substantially constant, the collagen tissue builds protuberances and therewith the thickness of the collagen tissue increases or grows, respectively. The treatment with the UVA light and by the respective focus point 13 allows a kind of microtreatment, such that the collagen tissue structure can be formed or shrunk in any direction according to the pattern and the applied local UVA energy. FIG. 3H depicts a situation of a skin volume 26a before a UVA light treatment and a different volume 26b of the same skin after the UVA light treatment, wherein the skin volume 26a and 26b remains the same, but has different shapes. The skin shrinks on the x-y plane and extends in the z direction of the thickness 36. The growth factor for the thickness is a growth factor shown by experience for a certain collagen thickness growing according to a certain applied UVA light energy or a respective UVA light energy density 39. At this point it shall be mentioned that the two terms UVA light energy and UVA light energy density 39 are equivalent, except that the energy is valid for a certain volume of the skin which can then be distributed as the pattern. Said growth factor is preferably derived from a plurality of experiments with different skin, with different patients, patients of different ages and with other different properties and is dependent on a plurality of patient parameters. Thus, preferably the growth factor for the treatment is adapted to the respective patient. In other words said growth factor is preferably derived from the fact that a unit of the UVA light energy causes a growth in thickness of the collagen tissue structure of for example 10 µm. But also a growth of new collagen is taken into account by a determination of the growth factor. Said growth factor or function, respectively, is not proportional to the growth in thickness 36. Preferably the function is calculated also as a function of the pattern how the focus point 13 with the calculated UVA light energy for the specific volume of the skin is moved over the skin to produce said pattern.

The processing and control unit 10 further determines a second light energy or intensity and a position or a path for the focus point 13, how and where the second light shall be applied to the skin. The same manual, automatic or semi-automatic control possibilities are provided to position the focus point 13 behind the aperture 8 as in the UVA light application.

The processing and control unit 10 preferably controls the UVA light source 3 and the second light source, such that the UVA light energy and/or the second light energy or intensity is applied to the skin as determined.

FIG. 1 shows also the focus point 13 being positioned on top of a layer 21c of the skin, consisting of a plurality of skin layers 21a-21e in that example, being partly collagen layers.

Figure 2:
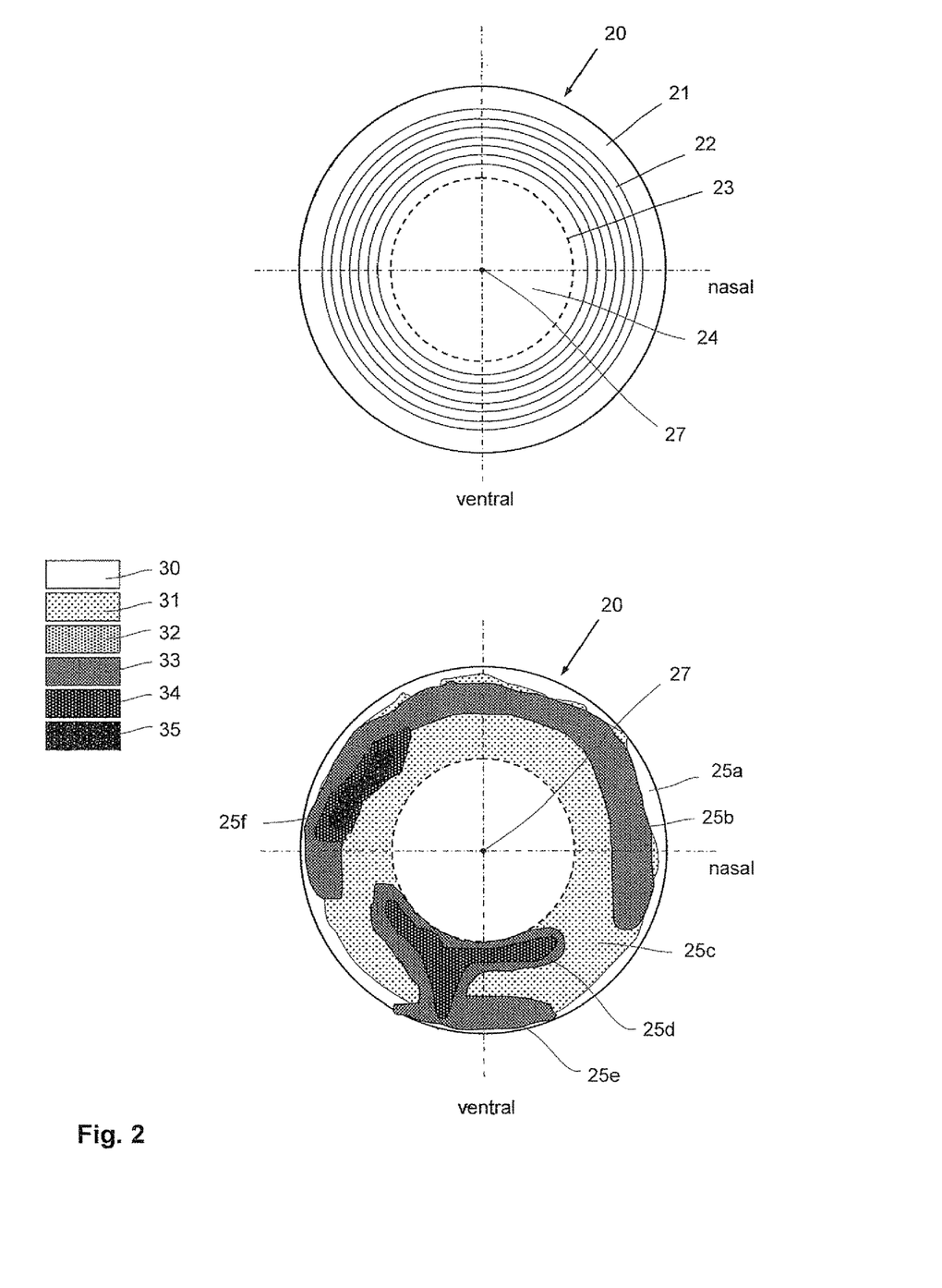
FIG. 2 in the upper part is a schematic drawing of the eye from a frontal view indicating the limbus and circular rings around a center axis of the eye, wherein the lower drawing indicates areas with different thicknesses of the sclera.

FIG. 2 in the upper part shows a schematic drawing of the eye 20 from a frontal view in the direction of the center axis 24 of the eye 20, showing the sclera and/or conjunctiva 21, indicating the limbus 23, the cornea 24 and a plurality of the circular ring shaped areas 22 around the center axis 24, which are preferably defined for calculation purposes.

FIG. 2 in its lower part shows another schematic drawing of the eye 20 in the same view from the front but with indicated different thicknesses 36 of the collagen in different regions 25a-f. FIG. 2 on the left side shows an indication table with different textures corresponding to different thickness deviation values 30-35. The texture is also indicated in the different regions 25a-f. The thickness 36 or the thickness deviation 37 of the respective eye 20 are displayed on the screen 11 preferably as in FIG. 2, lower part, or different, with different colors or the like. FIG. 2 depicts only an example of a display of the thickness deviation 37.

FIG. 3A is a schematic drawing of a top view of a certain collagen layer 21b of the sclera or conjunctiva 21 or the skin, respectively, wherein the orientation of the collagen fibers or the collagen fiber bundles is recognizable. The depicted collagen layer is preferably a cut part of the collagen tissue structure at any location and in any direction.

The focus point 13 describing the pattern or the respective UVA light energy is preferably positioned stepwise or continuously along a plurality of paths describing the pattern as a dot matrix or a lined matrix, wherein the plurality of paths are disposed:

in the form of parallel, orthogonally intersecting or circular paths within a plane or a spherical plane within the collagen tissue structure;

in the form of parallel, orthogonally intersecting or circular paths within a plurality of planes or spherical planes adjacent and parallel to each other within the collagen tissue structure;

in the form of parallel, orthogonally intersecting or circular paths within one collagen layer of the collagen tissue structure;

in the form of parallel, orthogonally intersecting or circular paths within two or more collagen layers, wherein the collagen layers are locally parallel to the surface of the eye; or in the form of a three-dimensional, volume like pattern adapted to the local collagen tissue structure.

FIGS. 3B-G are schematic drawings of different patterns as examples. FIGS. 3B-E are examples from a horizontal perspective on the x-y-plane parallel to the skin, wherein the black dots or lines indicate the light points or paths. FIGS. 3F-G are examples of a three-dimensional perspective, wherein in FIG. 3F a plurality of planes each containing a certain part of the pattern or in FIG. 3G three-dimensional parts of the pattern are arranged within the specific volume of the skin. The distances of the focus points 13 and light spots, respectively, according to FIG. 3B are preferably determined such that the distance is short enough to allow a crosslinking between the adjacent collagen fibrils and big enough to reduce the total UVA energy applied to a reasonable amount. In the example the UVA energy is about 20% of a different energy which would be applied if no focusing and blank areas would exist.

FIG. 3H is the schematic drawing of the skin volume 26a before and of the skin volume 26b after the treatment with the UVA light energy. It can be seen that by the tightening and shrinking of the collagen tissue in the x-y direction said volume remains equal but becomes higher or thicker.

Figure 4:
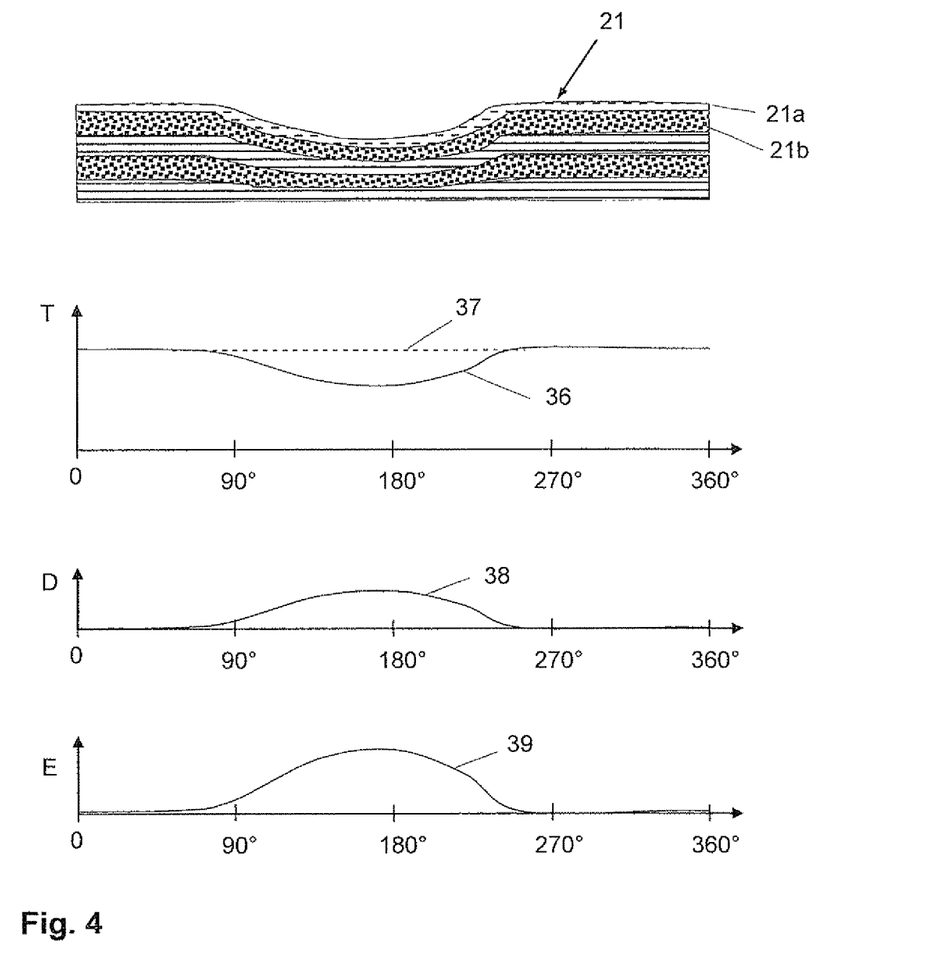
FIG. 4 is a schematic drawing of a side view or cross-sectional view, respectively, of the sclera or conjunctiva with a plurality of collagen layers on top of each other;
below is a graph T indicating the thickness as a function of the location;
below is a graph D indicating a thickness deviation as another function of the location;
below is a graph E indicating a determined energy density as a function of the location necessary for the growth of new collagen.

FIG. 4 is a schematic drawing of a side view or a cross-sectional view, respectively, of the skin showing again an example of the plurality of collagen layers arranged on top of each other. Below a graph T is shown indicating the thickness 36 around the eye 20 on a certain plane orthogonal to the center axis 24, and the determined target thickness 37 which is constant in this example. The abscissa is given in degrees around the center axis 24 of the eye 20. Below a corresponding graph D is shown indicating the thickness deviation 38. Again below a graph E is shown indicating the determined UVA light energy density 39 which is determined to be necessary for the crosslinking and growth of the respective collagen in order to reach the target thickness 37 in a certain ring shaped area of a respective plane of the eye 20, as depicted in FIG. 2. This is only an illustrative example of how the UVA light energy density 39 is preferably calculated. Preferably the UVA light energy or the UVA light energy density 39 is calculated as a three-dimensional graph.

The processing and control unit 10 is preferably adapted to determine a certain UVA light energy for the specific volume of the skin, wherein the certain UVA light energy is distributed according to the respective preferably selected pattern. The application of the certain UVA light energy to the skin is then preferably performed by moving the focus point 13 with the UVA light either in discrete steps or continuously along said certain pattern, such that the certain energy is distributed within said certain volume. As described above and depicted as examples in FIGS. 3B-G, said pattern is preferably a predefined pattern of one path or a plurality of parallel paths as one or more lines or rings or the like. The pattern can also be a single point, a matrix of points, a cross or a matrix of single crosses, or the like. The pattern is preferably within one or a plurality of planes or describes a three-dimensional spherical figure in the form of one or more cylinders or the like. Preferably one pattern layer is displaced on top of another pattern layer. The pattern can also be a 3D pattern over a certain volume, such that the certain UVA energy is distributed over different radial heights of the skin in the z direction, perpendicular to the surface of the eye 20.

The pattern has preferably the same orientation as the respective collagen fibers or the collagen fiber bundles within said certain volume. The one or more paths are preferably aligned with said orientation of the respective collagen fibers or the collagen fiber bundles, parallel or perpendicular to said orientation.

Preferably, the image processing unit 9 continuously detects said orientation of the new crosslinking or growing collagen tissue structure and adapts the pattern and paths for the UVA light energy thereto optimally. An adaptation algorithm adapts the new changing pattern and paths.

Preferably, the image processing unit 9 detects a continuous growth in thickness 36 and the new collagen tissue structure and adjusts the determined UVA light energy, such that a thickness-controlled crosslinking and preferably growth of the new collagen take place. By continuously determining the actual thickness 36 a precisely controlled target thickness is achievable.

Preferably, the processing and control unit 10 is adapted to apply the UVA light with the focus point 13 layer by layer, wherein one crosslinked collagen layer is generated on top of the previous crosslinked collagen layer.

Preferably, the imaging unit 2 and the image processing unit 9 are adapted to further recognize varicose vessels within the imaging volume. The processing and control unit 10 is preferably adapted to control the position or path of the focus point 13, such that it follows the varicose vessel in order to disintegrate it by the second light which is the Laser light. Preferably the second light energy or intensity is applied along the varicose vessel in an automatic or semi-automatic way. Preferably the focus point 13 can also be moved manually by the navigation control input means 12 along the varicose vessel. The second light is preferably generated by one or a plurality of pulses, which are controlled manually or in an automatic or semi-automatic way.

Preferably, the imaging unit 2 and the image processing unit 9 are adapted to further recognize end-arterioles within the imaging volume, wherein the Laser therapy system can be used for Laser Needling with the second light. The processing and control unit 10 is adapted to control the positioning of the focus point 13 at the respective end-arteriole and the application of the second light energy or intensity, such that the end-arteriole is denatured or perforated or such that an optical breakdown is induced in order to make the end-arteriole permeable for corpuscular blood cells and in particular for thrombocytes and to stimulate a growth of new collagen (Laser-Needling). The new collagen is also simply called collagen. It is also imaginable that the image processing unit 9 recognizes and localizes a plurality of end-arterioles, wherein the processing and control unit 10 controls the positioning of the respective focus point 13 and the second light energy or intensity at the respective end-arteriole of the plurality of end-arterioles in an automatic or semi-automatic way. Preferably the image processing unit 9 recognizes then a respective turning point of the respective end-arteriole and positions the focus point 13 at the respective turning point.

Preferably, the processing and control unit 10 is further adapted to determine the target thickness 37 as a function of a maximum or an average value of the thickness 36 within the ring shaped area 22. Different examples of the ring shaped area 22 are given in FIG. 22 at the top. Another preferred embodiment calculates the target thickness 37 as a function of at least one input value of the user and/or as a maximum value for the target thickness 37. Another preferred embodiment calculates the target thickness 37 as a certain percentage or a maximum value for a determined growth of the new collagen and due to the crosslinking. Thus, the specific percentage of the growth in thickness 36 is generated by the UVA light treatment and the difference to one hundred percent is treated by the Laser Needling method with the second light. Another preferred embodiment calculates the target thickness 37 as a function of one or more of the above-mentioned parameters or values. Preferably, the target thickness 37 is calculated as a three-dimensional function, taking also a physiological standard thickness into account. The physiological standard thickness is preferably an average thickness of a healthy eye 20.

Preferably, the processing and control unit 10 is further adapted to receive refractive data of the eye 20 and to calculate the target thickness 37 such that a desired refractive correction for the eye 20 to be achieved is determined. For the refractive correction the skin of the eye 20 and thus the collagen tissue have to be strengthened at certain positions according to an expert data base. The target thickness is preferably achieved by the UVA light treatment as described above. Preferably in a second step the Laser Needling treatment is applied as well.

Preferably, the imaging unit 2 and the image processing unit 9 are adapted to recognize and detect colors, such that local parts of the skin are detected having a color deviation from a stored, an averaged or an input color value. From the color deviation a required collagen growth is determined as a function of the color deviation. Thus the respective target thickness 37 is determined as a function of at least the thickness 36 and said required crosslinking or thickness growth.

Preferably, the image processing unit 9 and the processing and control unit 10 are further adapted to recognize parts within the skin which are already treated or which are not yet treated by the Laser therapy system. Preferably said treated and non-treated parts are indicated on the screen 11 in different colors. Preferably the processing and control unit 10 applies the UVA or the second light only to such parts of the skin which are not yet treated or not sufficiently treated.

Preferably, the image processing unit 9 is adapted to determine and to detect at least one reference point within the skin, and to use the at least one reference point to refer the thickness 36 to a coordinate system of the eye 20. The at least one reference point can also be used for image stitching. Also the target thickness 37, the UVA light energy or the second light energy or intensity and the focus point 13 can be set in relation to the at least one reference point.

Preferably the UVA light is generated by two different light beams with a wavelength double the wavelength of the generated UVA light, such that the two different light beams or photons overlap within a few femto-seconds and generate substantially the UVA light with the half wavelength. Preferably the resulting wavelength of the UVA light lies between 300-450 nm. Preferably the UVA light source 3 is a light source for a one photon excitation. For a two photon excitation with the respective two different light beams or photons the respective light source is a femto-second laser.

Preferably the Laser light source is a femto-second Laser.

It shall be mentioned again, that the recognition of the collagen fibers within the skin and growth of the new collagen is preferably detected three-dimensionally.

A method for treatment of a sclera and/or conjunctiva 21 of the living eye with the Laser therapy system comprises the following steps:

a) applying to the eye onto the sclera and/or conjunctiva 21 by the dispenser 1 the agent containing a photosensitizer for mediating a collagen and elastin crosslinking for a growth of a collagen tissue structure during a treatment with UVA light;

b) recording 3D images of the sclera and/or conjunctiva 21 within an imaging volume by the imaging unit 2 generating respective image data;

c) recognizing the collagen tissue structure and determining a thickness 36 of said collagen tissue structure as a function of position by the image processing unit 9 receiving the image data;

d) determining a target thickness 37 for the thickness 36 as another function of position by an input or by comparison with stored reference eye data;

e) determining a thickness deviation 38 as a difference between the target thickness 37 and the thickness 36;

f) determining an UVA light energy pattern as a further function of position, of the thickness deviation 38 and of a growth factor for the thickness 36 under the UVA light energy pattern, such that an application of the UVA light energy pattern is assumed to effect a growth of the collagen tissue structure until the target thickness 37 is achieved;

g) applying said UVA light energy pattern locally to the sclera and/or conjunctiva 21 by the Laser therapy system, wherein UVA light is controlled and optically focused to a focus point 13 which is controllably moved within the sclera and/or conjunctiva 21 such that said UVA light energy pattern is applied therein.

Preferably in step (c) there are further detected by the image processing unit 9 single collagen fibers and a net of said single collagen fibers within the collagen tissue structure, wherein the UVA light energy pattern is determined such that the pattern is adapted to said net of said single collagen fibers, such that in step (g) the focus point 13 is controlled to follow lines corresponding to said net of said single collagen fibers.

Preferably in an additional step varicose blood vessels are detected by the image processing unit 9, and the second focused Laser light with the second wavelength and a second energy from the Laser light source 4 is applied to said varicose blood vessels, wherein the second energy is controlled such that the varicose blood vessels get eroded.

Preferably the Laser therapy system determines parts of the sclera and/or conjunctiva which have been already treated by the UVA light, whereupon in a following UVA light treatment step these parts are spared.

Additionally a treatment may be done also as described before within the description of the Laser therapy system.

REFERENCE SIGNS 1 dispenser
2 imaging unit
3 UVA light source
4 Laser light source
5 optical system
6 optical deflection and focusing unit
7 actuator unit
8 aperture
8b contact lens
8c coupling gel
9 image processing unit
10 processing and control unit
11 screen
12 navigation control input means
13 focus point
20 eye
21 sclera or conjunctiva of the eye (=skin)
21a-21e skin layer
22 ring shaped area
23 limbus
24 cornea
25a-f region
26 optical path
26a skin volume before UVA light treatment
26b skin volume after UVA light treatment
27 center axis of the eye 20
30-35 deviation value
36 thickness
37 target thickness
38 thickness deviation
39 UVA light energy
D graph of the thickness deviation 38
E graph of the light energy density 39
T graph of the thickness 36
X, Y, Z coordinates

The invention claimed is:

1. A laser therapy system for treatment of a sclera and/or conjunctiva of a living eye, comprising:

a) a dispenser for dispensing an agent on the sclera and conjunctiva, the agent containing a photosensitizer and mediating a collagen and elastin crosslinking for a growth of a collagen tissue structure in a targeted manner during a treatment with a UVA light;

b) an imaging unit for 3D imaging of the sclera and/or conjunctiva within an imaging volume, outputting image data;

c) an image processing unit adapted to receive the image data, to recognize the collagen tissue structure and to determine a thickness of said collagen tissue structure as a function of a position;

d) a UVA light source which is controllable and generates the UVA light with a first wavelength adapted to activate the collagen and elastin crosslinking in the sclera and/or conjunctiva in combination with the photosensitizer dispensed on the sclera and/or conjunctiva;

e) a second light source as laser light source which is controllable and generates a second light with a second wavelength adapted to be absorbed mainly by varicose blood vessels and end-arterioles;

f) an optical system coupled to the imaging unit as well as to the UVA and to the second light source; the optical system having an aperture to the eye as an outlet for the UVA light and for the second light and as an inlet for light irradiated from the imaging volume in the sclera and/or conjunctiva guided by the optical system to the imaging unit, the optical system providing controllable deflection and focusing means deflecting and focusing the UVA light and the second light to a focus point behind the aperture, wherein said focus point is controllably positionable within the imaging volume; and g) a processing and control unit adapted
to determine a target thickness of the collagen tissue structure as another function of the position and to determine a thickness deviation of the collagen tissue structure as a difference between the target thickness of the collagen tissue structure and the thickness of the collagen tissue structure;

to determine a pattern for an application of a local UVA light energy, wherein said pattern is described by the focus point in the sclera and/or conjunctiva;

to determine the UVA light energy as a further function of the position, of the thickness deviation of the collagen tissue structure, the pattern and a growth factor for the thickness of the collagen tissue structure, such that the application of the UVA light energy is assumed to effect the growth of the collagen tissue structure until the target thickness of the collagen tissue structure is achieved; and to control the optical system, the UVA light source and the second light source, such that the UVA light energy and the second light energy or intensity are applied to the sclera and/or conjunctiva as determined.

2. The laser therapy system according to claim 1, wherein the focus point for the application of the UVA light energy is positioned stepwise or continuously along a plurality of paths describing the pattern as a dot matrix or a lined matrix, wherein the plurality of paths are disposed in the form of parallel, orthogonally intersecting or circular paths within a plane or a spherical plane within the collagen tissue structure;

in the form of parallel, orthogonally intersecting or circular paths within a plurality of planes or spherical planes adjacent and parallel to each other within the collagen tissue structure;

in the form of parallel, orthogonally intersecting or circular paths within one collagen layer of the collagen tissue structure;

in the form of parallel, orthogonally intersecting or circular paths within two or more collagen layers, wherein the collagen layers are locally parallel to the surface of the eye; or in the form of a three-dimensional volume like pattern adapted to the local collagen tissue structure.

3. The laser therapy system according to claim 1, wherein the image processing unit is configured to determine further an orientation of respective collagen fibers or collagen fiber bundles within a respective collagen layer of the collagen tissue structure, and wherein the processing and control unit is adapted to align the pattern to the determined orientation of the respective collagen fibers or collagen fiber bundles.

4. The laser therapy system according to claim 3, wherein the image processing unit is configured to continuously determine the orientation of the collagen fibers or collagen fiber bundles of the collagen tissue structure, and wherein the processing and control unit is configured to adapt the pattern and paths for the UVA light energy to the determined orientation of the collagen fibers or collagen fiber bundles of the collagen tissue structure according to an adaptation algorithm.

5. The laser therapy system according to claim 1, wherein the image processing unit is adapted to continuously determine the growth in thickness of the collagen tissue structure and wherein the processing and control unit is configured to adjust the determined UVA light energy, such that the thickness of the collagen tissue structure grows in a controlled way, accordingly.

6. The laser therapy system according to claim 1, wherein the imaging unit and the image processing unit are adapted to further recognize varicose vessels within the imaging volume; and the processing and control unit is further adapted to control the position or path of the focus point and the second light energy or intensity along the varicose vessel in a manual, an automatic or semi-automatic way for a disintegration of the varicose vessel.

7. The laser therapy system according to claim 1, wherein the imaging unit and the image processing unit are adapted to further recognize end-arterioles within the imaging volume; and the processing and control unit is further adapted to control the positioning of the focus point at the respective end-arteriole and the second light energy or intensity, such that the end-arteriole is denatured or perforated or an optical breakdown is induced in order to make the end-arteriole permeable for corpuscular blood cells and to stimulate a growth of new collagen.

8. The laser therapy system according to claim 7, wherein the image processing unit is adapted to recognize and localize a plurality of end-arterioles, and wherein the processing and control unit is further adapted to control the positioning of the respective focus point and the second light energy or intensity at the respective end-arteriole of the plurality of end-arterioles in an automatic or semi-automatic way.

9. The laser therapy system according to claim 1, wherein the processing and control unit is further adapted to determine the target thickness of the collagen tissue structure as a function of at least a maximum or an average value of the thickness of the collagen tissue structure within at least one ring shaped area;

at least one input value of a user, a maximum value for the target thickness of the collagen tissue structure;

a percentage or a maximum value for a collagen growth induced by the UVA light in comparison with the target thickness of the collagen tissue structure which has to be reached, such that the rest percentage is to be grown by a treatment with the second light;

other values or functions; or a combination thereof.

10. The laser therapy system according to claim 1, wherein the processing and control unit is further adapted to receive refractive data of the eye and to calculate from them a desired refractive correction of the eye;

to determine the required growth of the collagen tissue structure and the growth of new collagen, such that the refractive correction of the eye is achieved; and to determine the target thickness of the collagen tissue structure and the second light energy or intensity and paths for the focus point for a laser needling treatment.

11. The laser therapy system according to claim 1, wherein the imaging unit and the image processing unit are adapted to recognize and detect colors and to detect local parts of the sclera or conjunctiva having a color deviation different from a stored, an averaged or an input color value;

to determine a required crosslinking and the target thickness of the collagen tissue structure as a function of the color deviation and the thickness of the collagen tissue structure; and to determine the second light energy or intensity and paths for the focus point for a laser needling treatment as a function of the color deviation.

12. The laser therapy system according to claim 1, wherein the imaging unit is based either on an Optical Coherence Tomography (OCT), a fluorescence or self-fluorescence microscopy, a fluorescence or self-fluorescence tomography, a light reflection or a light extinction measurement with one or more wavelengths for discrimination between collagen and blood vessels, comprises polarization filters, or is a combination thereof.

13. The laser therapy system according to claim 1, wherein the image processing unit and/or the processing and control unit are further adapted to recognize already treated and non-treated parts of the sclera and/or conjunctiva by the UVA light or by the second light, wherein
- only the non-treated parts or not sufficiently treated parts are further treated by the UVA light or the second light, or
- the treated and non-treated parts are displayed in different colors on a screen, and/or
- wherein the optical system comprises at least one moveable part, wherein the aperture is controllably moveable over the sclera and/or conjunctiva either manually or controllably actuated by the processing and control unit.

14. The laser therapy system according to claim 1, wherein the image processing unit is adapted
- to determine and to detect at least one reference point within the sclera and/or conjunctiva, and
- to use the at least one reference point for image stitching or to refer the thickness of the collagen tissue structure, the target thickness of the collagen tissue structure, the UVA light energy or the second light energy or intensity and the focus point to the at least one reference point.

15. The laser therapy system according to claim 1, wherein the agent is a cream, a gel or a liquid with the effect of penetrating the skin and contains a Photosensitizer like riboflavin (vitamin B2), and/or
- wherein the agent contains coenzymes for a synthesis of collagen and elastin, namely vitamin A, vitamin E and/or vitamin C, and/or
- wherein the photosensitizer containing agent is fluorescent for determining the penetration depth into the skin and/or
- wherein the aperture comprises an integral or a non-integral contact lens for an optical coupling with the eye, wherein a side of the contact lens directed towards the eye has a concave form being adapted to the eye and being either of glass, of a coupling gel or of a flexible pocket with a liquid or a coupling gel inside to optically adapt to the eye, and/or
- wherein the aperture comprises an integral or a non-integral contact lens for an optical coupling with the eye, wherein a middle part of the contact lens above the cornea is opaque for the UVA and the second light, and/or
- wherein the aperture comprises a surrounding ring shaped means or container being adapted to be placed on the eye and to be filled with an immersion liquid above the eye, such that the UVA light or another light is led from the aperture through the immersion liquid towards the eye.

* * * * *